United States Patent [19]

Tasaka et al.

[11] 3,959,394

[45] May 25, 1976

[54] PROCESS FOR SELECTIVE METHYLATION OF PHENOLS

[75] Inventors: Akira Tasaka, Takatsuki; Akio Fukui, Ibaragi; Akira Morii; Masahiro Fujiwara, both of Takatsuki, all of Japan

[73] Assignee: Sumitomo Chemical Company Limited, Osaka, Japan

[22] Filed: Sept. 4, 1975

[21] Appl. No.: 610,186

Related U.S. Application Data

[63] Continuation of Ser. No. 369,003, June 11, 1973, abandoned.

[30] Foreign Application Priority Data

June 12, 1972 Japan............................... 47-58788

[52] U.S. Cl............................. 260/621 R; 252/462; 252/475; 260/624 C; 260/626 R; 260/626 T
[51] Int. Cl.²......................................... C07C 37/16
[58] Field of Search............... 369/3; 252/462, 475; 260/621 R, 624 C, 626 T, 619 R, 620

[56] References Cited
UNITED STATES PATENTS

3,347,936 10/1967 Froitzheim et al............. 260/621 R
3,645,915 2/1972 Stiles................................. 252/462
3,701,811 10/1972 Nicklin........................... 260/621 R
3,790,641 2/1974 Oshima et al................... 260/621 R

FOREIGN PATENTS OR APPLICATIONS

29,293 9/1970 Japan............................ 260/621 R

*Primary Examiner*—Norman Morgenstern
*Attorney, Agent, or Firm*—Stevens, Davis, Miller & Mosher

[57] ABSTRACT

Phenols such as phenol, o-cresol, m-cresol, p-cresol, xylenols, ethylphenol, propylphenol, and butylphenol are selectively methylated in ortho-position with methanol in the vapour phase at an elevated temperature, for example, 300° to 500°C, under a pressure of 0.5 to 20 atmospheres absolute at a space velocity of 100 to 2000 hr$^{-1}$ in the presence of a three-component catalyst consisting of cerium oxide, magnesium oxide and germanium oxide, or a four-component catalyst consisting of cerium oxide, magnesium oxide, germanium oxide and tin oxide.

16 Claims, No Drawings

PROCESS FOR SELECTIVE METHYLATION OF PHENOLS

This is a continuation of application Ser. No. 369,003, filed June 11, 1973 now abandoned.

This invention relates to a process for the methylation in ortho-position of phenols having at least one hydrogen atom in the ortho-position.

More particularly, the invention pertains to a process for the selective methylation in ortho-position of phenols represented by formula:

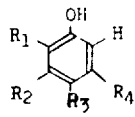

wherein each of $R_1$, $R_2$, $R_3$ and $R_4$ which may be the same or different, represents a hydrogen atom or a saturated aliphatic hydrocarbon group having 1 - 6 carbon atoms, especially 1 to 4 carbon atoms, such as methyl, ethyl, isopropyl, tert-butyl, etc., where the phenols are methylated with methanol in the vapor phase at an elevated temperature in the presence of a catalyst, which comprises using a catalyst containing three components of cerium oxide, magnesium oxide and germanium oxide or a catalyst containing four components of cerium oxide, magnesium oxide, germanium oxide and tin oxide.

It is known that catalysts containing cerium oxide and magnesium oxide are effective in the methylation of ortho-position of phenols having at least one hydrogen atom at the ortho-position in the vapour phase and at an elevated temperature with methanol. That is to say, some of the present inventors disclosed in Japanese Pat. publication No. 29293/70 that phenols methylated at the ortho-position could be obtained in the presence of said two-component catalyst with selectivity of 95% or more, based on the consumed raw phenol. However, it is apparent that there are still a few disadvantages in said prior art process. For example, (1) conversion of the phenols is not satisfactory, (2) methanol decomposition takes place so considerably that methanol utilization efficiency is not sufficient, (3) when 2,6-dimethyl phenol derivatives are desired to produce from phenols having hydrogen atoms in two ortho-positions, their yield is low.

As a result of studies on improvement of these disadvantages, the present inventors have found that catalysts containing three components of cerium oxide, magnesium oxide and germanium oxide, or catalysts containing four components of cerium oxide, magnesium oxide, germanium oxide and tin oxide can satisfactorily meet the desired purpose, and have a good performance.

Comparison of performances of a catalyst of cerium oxide-magnesium oxide-germanium oxide ($CeO_2$—MgO—$GeO_2$), a catalyst of cerium oxide-magnesium oxide-germanium oxide-tin oxide ($CeO_2$—MgO—$GeO_2$—$SnO_2$), and catalysts of cerium oxide-magnesium oxide ($CeO_2$—MgO) is given in Table 1.

Reaction conditions:

Reaction pressure: atmospheric
Molar ratio of phenol to methanol = 1 : 6
Gas space velocity: 1000 hr$^{-1}$ The expressions used in Table 1 are defined in the following equation:

Phenol conversion (%)

$$= \frac{\text{Phenol consumed in the reaction (mole/hr.)}}{\text{Phenol supplied to the reaction (mole/hr.)}} \times 100$$

o-Cresol yield (%)

$$= \frac{\text{o-Cresol formed in the reaction (mole/hr.)}}{\text{Phenol supplied to the reaction (mole/hr.)}} \times 100$$

Methanol utilization efficiency (%)

$$= \frac{\text{O-Cresol formed in the reaction (mole/hr.)} + 2,6\text{-xylenol produced in the reaction (mole/hr.)} \times 2}{\text{Methanol consumed in the reaction (mole/hr.)}} \times 100$$

2,6-Xylenol yield is defined in the same manner as defined as to the o-cresol yield.

Table 1

| Catalyst (ratio by weight) | $CeO_2$—MgO—$GeO_2$ (1:0.7:0.1) | | $CeO_2$—MgO (1:0.7) | | $CeO_2$—MgO—$GeO_2$—$SnO_2$ (1:0.5:0.1:0.2) | | $CeO_2$—MgO (1:0.5) | |
|---|---|---|---|---|---|---|---|---|
| Reaction temp. (°C) | 425 | 450 | 425 | 450 | 425 | 450 | 425 | 450 |
| Phenol convertion (%) | 87 | 92 | 52 | 80 | 87 | 92 | 49 | 79 |
| o-Cresol yield (%) | 24 | 17 | 40 | 58 | 22 | 16 | 35 | 54 |
| 2,6-Xylenol yield (%) | 57 | 71 | 10 | 19 | 63 | 72 | 10 | 18 |
| Methanol utilization efficiency (%) | 55 | 45 | 43 | 33 | 50 | 36 | 40 | 26 |

As is apparent from Table 1, the catalysts of three components, cerium oxide-magnesium oxide-germanium oxide, and four components, cerium oxide-magnesium oxide-germanium oxide-tin oxide, have the following remarkable effects, as compared with the catalysts of two components, cerium oxide-magnesium oxide:

1. Phenol conversion is increased by 10 - 40 %.
2. Methanol utilization efficiency is increased by 10 - 12 %.
3. Yield of dimethyl phenol derivatives is increased by about 50 %.

These effects bring about great advantages in synthesizing useful phenol derivatives according to the present reaction; particularly in synthesizing 2,6-dimethyl phenol derivatives.

Typical examples of phenols used in the present invention include phenol, o-cresol, m-cresol, p-cresol, xylenols (excluding 2,6-xylenol), various ethylphenols, propylphenols, butylphenols, etc. including mixtures of any of these, e.g., phenol and o-cresol. Ortho-methylation products include o-cresol, 2,6-xylenol, 2,3,6-trimethylphenol, 2-methyl-4-tert. butylphenol, etc. These products are industrially important compounds as intermediates for synthetic resins, medicaments and stabilizers.

The catalysts of the present invention contain three components, i.e., cerium oxide, magnesium oxide and germanium oxide or four components i.e., cerium oxide, magnesium oxide, germanium oxide and tin oxide, and the proportions of individual components in the mixed oxide depends upon the desired product in the present reaction, but a mixing ratio by weight of magnesium oxide to cerium oxide of 0.1 - 2 : 1, preferably 0.5 - 1 : 1, a mixing ratio by weight of germanium oxide to cerium oxide of 0.01 - 2 : 1, preferably 0.05 - 1 : 1, and a mixing ratio by weight of tin oxide to cerium oxide of 0.01 - 2 : 1, preferably 0.05 - 1 : 1 are suitable for the present invention.

The catalyst may be prepared according to the ordinary method for preparing metallic oxide catalysts, but a coprecipitation method for preparing a particularly homogeneous oxide mixture is suitable for the preparation of the catalyst. In the latter case, a hydroxide mixture of the components formed by the coprecipitation is calcined at a temperature of 500° to 800°C to prepare a mixed oxide catalyst. Furthermore, the present catalyst may be prepared in the form of tablets by incorporating an inactive carrier and then shaping, or may be supported on an inert carrier such as calcined alumina, diatomaceous earth, kaolin, graphite, etc., according to the ordinary method.

The catalyst may be further modified by adding other metallic oxide than the above-mentioned components to the catalyst. Even if the present catalyst includes oxides of cerium homologs, for example, rare earth elements such as lanthanum, neodymium, etc., the performance of the catalyst is not so greatly changed. However, in a case of using a mixture of oxides of rare earth elements in place of cerium oxide as an essential component, these oxides mixture should contain at least about 30 % by weight of cerium oxide.

Reaction conditions employed in the present process are given as follows:

| Reaction temperature: | 300° - 500°C, preferably 350° - 450°C |
| Reaction pressure: | 0.5 - 20 atmospheres (absolute), preferably 1 - 10 atmospheres (absolute) |
| Molar ratio of feed methanol to feed phenol: | 1 - 15 : 1, preferably 2 - 10 |
| Gas space velocity: | 100 - 2000 hr$^{-1}$ (in terms of 0°C, 1 atm, packings - free column), preferably 200 - 1000 hr$^{-1}$ |

The type of reactor employed may be any of the fixed bed or fluidized bed types. In the present reaction, however, it is sufficient to adopt a fixed bed reactor which is simple in operation.

It is one of the features of the present catalysts that there is less change in performance during the service time, and thus the present catalysts can withstand prolonged service. When an activity is lowered in the service for several months, the activity of the present catalysts can be regenerated by passing air or steam containing 20 % or less of oxygen through the catalysts.

The mixture of phenols resulting from the reaction is subjected to distillation to remove methanol, water, etc., contained therein, and then subjected to purification of the conventional procedure to obtain the desired product at a high purity. Since by-products other than the ortho-methylated products are much less in yield, the purification is very simple, which is also another distinguished advantage of the present invention.

When the present catalyst is employed, it is relatively easy to obtain an ortho-dimethyl compound from a phenol having 2 hydrogen atoms in the ortho-positions. When it is desired to obtain the ortho-dimethyl compound alone, this can be easily done by recycling to the reactor a ortho-monomethyl compound, which is a reaction intermediate and is separated from the desired reaction product, together with the feed phenol. Consequentially, in such process the overall yield of the desired product can be increased.

The present invention will be described in detail by way of examples, but the present invention will not be limited to these examples.

In the following examples, the conversion, yield, etc., have the same meanings as defined above.

EXAMPLE 1

2.2 g of germanium chloride (GeCl$_4$), 116.9 g of ammonium ceric nitrate [Ce(NO$_3$)$_4$.2NH$_4$NO$_3$.2H$_2$O] and 152.7 g of magnesium nitrate (Mg(NO$_3$)$_2$.6H$_2$O) were dissolved in 1.5 l of water, and admixed with 700 cc of 28 % aqueous ammonia solution at 50°C with stirring. The resulting precipitates of hydroxide mixture were filtered, washed, dried at 120°C and then calcined in air at 600°C for 3 hours. The resulting oxide mixture was pulverized, admixed with 2 g of graphite as a lubricant and shaped, whereby 57 g of cylindrical catalysts, 5 mm in diameter and 5 mm in height, were obtained.

Twenty c.c. of the catalysts thus prepared were filled in a quartz reactor tube, 18 mm in inner diameter, and heated externally in an electric oven. A solution of phenol and methanol at a molar ratio of phenol to methanol of 1 : 6 was supplied to the reactor tube through a preheater at a rate of 36.5 g per hour (gas space velocity: 1000 hr$^{-1}$). The reaction products were collected in a dry ice - acetone trap, and analyzed by gas chromatograph. Conversion, yields, etc., were calculated according to the definition as mentioned above. The results of the reaction are given in Table 2.

EXAMPLES 2 to 7

Catalysts were prepared in the same manner as in Example 1, except that the amounts of germanium chloride and magnesium nitrate were so changed that ratios by weight of GeO$_2$/CeO$_2$ might be 0.06 - 0.6, and ratios by weight of MgO/CeO$_2$ 0.5 - 0.9, and subjected to the same activity test as in Example 1. The compositions of the catalysts prepared and the results of the reaction are given in Table 2.

EXAMPLE 8

A catalyst having a ratio by weight of CeO$_2$ : La$_2$O$_3$ : Nd$_2$O$_3$ : MgO : GeO$_2$ of 0.8 : 0.1 : 0.1 : 0.7 : 0.1 was prepared in the manner similar to that of Example 1, and subjected to the same activity test as in Example 1. The results of the reaction are given in Table 2.

EXAMPLE 9

A catalyst having a ratio by weight of CeO$_2$ : La$_2$O$_3$ : Pr$_2$O$_3$ : Nd$_2$O$_3$ : Sm$_2$O$_3$ : MgO : GeO$_2$ of 0.5 : 0.24 : 0.06 : 0.18 : 0.02 : 0.5 : 0.1 was prepared in the manner similar to that of Example 1, and subjected to the same activity test as in Example 1. The results of the reaction are given in Table 2.

EXAMPLE 10

5.2 g of tin tetrachloride ($SnCl_4$), 8.6 g of germanium chloride ($GeCl_4$), 116.9 g of ammonium ceric nitrate [$Ce(NO_3)_4 \cdot 2NH_4NO_3 \cdot 2H_2O$] and 101.8 g of magnesium nitrate [$Mg(NO_3)_2 \cdot 6H_2O$] were dissolved in 1.5 l of water, and a catalyst was prepared from the solution in a manner similar to that of Example 1. The composition of the catalyst prepared and the results of the reaction are given in Table 3.

EXAMPLES 11 – 16

Catalysts having ratios by weight of $SnO_2/CeO_2$ of 0.1 – 0.4, $GeO_2/CeO_2$ of 0.06 – 0.3 and $MgO/CeO_2$ of 0.5 – 0.7 were prepared by changing the amounts of tin tetrachloride, germanium chloride and magnesium nitrate in the manner similar to that of Example 1, and subjected to the same activity test as in Example 1. The compositions of the catalysts thus prepared and the results of the reaction are given in Table 3.

EXAMPLE 17

A catalyst having a ratio by weight of $CeO_2 : La_2O_3 : Nd_2O_3 : MgO : GeO_2 : SnO_2$ of 0.8 : 0.1 : 0.1 : 0.5 : 0.1 : 0.2 was prepared in the manner similar to that of Example 1, and subjected to the same activity test as in Example 1. The results of the reaction are give in Table 3.

Table 2

| Example No. | | 1 | 2 | 3 | 4 | 5 | 6 | 7 | 8 | 9 |
|---|---|---|---|---|---|---|---|---|---|---|
| | | | | | Methylation reaction of phenol | | | | | |
| Catalyst composition (by weight) | $CeO_2$ | 1 | 1 | 1 | 1 | 1 | 1 | 1 | 0.8 | In addition: $La_2O_3$ 0.1 $Nd_2O_3$ 0.1 — 0.5 0.5 0.1 | In addition: $La_2O_3$ 0.24 $Pr_2O_3$ 0.06 $Nd_2O_3$ 0.18 $Sm_2O_3$ 0.02 |
| | MgO | 0.7 | 0.7 | 0.7 | 0.7 | 0.7 | 0.5 | 0.9 | 0.7 | | |
| | $GeO_2$ | 0.03 | 0.06 | 0.1 | 0.3 | 0.6 | 0.1 | 0.1 | 0.1 | | |
| Phenol conversion (%) | 425°C | 38.6 | 80.6 | 87.0 | 82.6 | 84.1 | 87.1 | 88.8 | 80.9 | | 80.7 |
| | 450°C | 87.0 | 89.7 | 92.4 | 88.6 | 92.8 | 90.1 | 94.0 | 87.8 | | 87.7 |
| o-Cresol yield (%) | 425°C | 33.6 | 29.4 | 23.7 | 15.1 | 19.1 | 21.8 | 27.3 | 25.2 | | 26.5 |
| | 450°C | 36.3 | 21.3 | 16.7 | 12.9 | 11.8 | 19.1 | 19.1 | 20.6 | | 22.7 |
| 2,6-Xylenol yield (%) | 425°C | 4.2 | 45.9 | 56.7 | 62.3 | 59.9 | 59.8 | 53.5 | 50.1 | | 49.4 |
| | 450°C | 47.5 | 64.9 | 71.2 | 70.1 | 75.2 | 67.3 | 69.6 | 62.6 | | 60.1 |
| o-Methylation selectivity* (%) | 425°C | 99.5 | 95.0 | 93.0 | 93.8 | 93.9 | 93.7 | 91.0 | 93.1 | | 94.1 |
| | 450°C | 96.3 | 96.2 | 95.3 | 93.7 | 93.8 | 94.9 | 94.4 | 94.7 | | 94.4 |
| Methanol utilization efficiency | 425°C | 48.3 | 65.0 | 55.1 | 43.0 | 59.0 | 41.0 | 51.5 | 46.5 | | 40.7 |
| | 450°C | 37.6 | 38.3 | 45.0 | 34.8 | 43.5 | 35.2 | 42.9 | 36.9 | | 33.7 |

$$\text{*o-Methylation selectivity (\%)} = \frac{\text{Amount of o-cresol formed (mole/hr)} + \text{Amount of 2,6-xylenol formed (mole/hr)}}{\text{Amount of phenol consumed in reaction (mole/hr)}} \times 100$$

Table 3

| Example No. | | 10 | 11 | 12 | 13 | 14 | 15 | 16 | 17 |
|---|---|---|---|---|---|---|---|---|---|
| | | | | Methylation reaction of phenol | | | | | |
| Catalyst composition (by weight) | $CeO_2$ | 1 | 1 | 1 | 1 | 1 | 1 | 1 | 0.8 In addition $La_2O_3$ 0.1 $Nd_2O_3$ 0.1 |
| | MgO | 0.5 | 0.5 | 0.7 | 0.7 | 0.7 | 0.5 | 0.5 | 0.5 |
| | $GeO_2$ | 0.1 | 0.1 | 0.1 | 0.1 | 0.1 | 0.06 | 0.3 | 0.1 |
| | $SnO_2$ | 0.1 | 0.2 | 0.1 | 0.2 | 0.4 | 0.2 | 0.2 | 0.2 |
| Phenol conversion (%) | 425°C | 76.3 | 86.7 | 83.2 | 82.0 | 76.4 | 78.5 | 81.4 | 81.2 |
| | 450°C | 82.4 | 91.7 | 89.5 | 88.9 | 84.7 | 89.0 | 86.7 | 89.0 |
| o-Cresol yield (%) | 425°C | 24.4 | 22.4 | 24.0 | 23.2 | 25.1 | 35.3 | 15.8 | 31.7 |
| | 450°C | 21.2 | 16.0 | 19.9 | 19.3 | 21.4 | 26.0 | 11.5 | 22.7 |
| 2,6-Xylenol yield (%) | 425°C | 50.1 | 60.9 | 56.1 | 55.9 | 46.9 | 41.1 | 60.2 | 45.3 |
| | 450°C | 58.0 | 72.4 | 67.2 | 66.4 | 58.3 | 60.9 | 69.1 | 61.5 |
| o-Methylation selectivity* (%) | 425°C | 97.5 | 96.0 | 96.3 | 96.5 | 94.2 | 97.3 | 93.4 | 94.8 |
| | 450°C | 96.1 | 96.4 | 97.2 | 96.4 | 94.2 | 97.6 | 93.0 | 94.6 |
| Methanol utilization efficiency (%) | 425°C | 39.5 | 50.3 | 40.1 | 38.4 | 38.6 | 55.0 | 43.2 | 50.2 |
| | 450°C | 32.1 | 36.3 | 32.8 | 31.6 | 32.5 | 37.3 | 35.6 | 39.9 |

$$\text{*o-Methylation selectivity (\%)} = \frac{\text{Amount of o-cresol formed (mole/hr)} + \text{Amount of 2,6-xylenol formed (mole/hr)}}{\text{Amount of phenol consumed in reaction (mole/hr)}} \times 100$$

EXAMPLE 18 m-Cresol was methylated with methanol, using the catalyst of $CeO_2$—MgO—$GeO_2$ having a ratio by weight of $CeO_2 : MgO : GeO_2$ of 1 : 0.7 : 0.7 : 0.1, prepared in Example 3. The reaction conditions and the result of the reactions are given below:

| | |
|---|---|
| Catalyst used (in volume): | 20 cc |
| Molar ratio of feeds: | methanol/m-cresol = 6 |
| Reaction temperature: | 450°C |
| Gas space velocity: | 1000 hr$^{-1}$ |
| m-Cresol conversion: | 100.0% |
| 2,3-Xylenol yield: | 3.5 % |
| 2,5-Xylenol yield: | 6.6 % |
| 2,3,6-Trimethylphenol yield: | 81.9 % |
| o-Methylation selectivity: | 92.0 % |
| Methanol utilization efficiency: | 33.7 % |

EXAMPLE 19 m-Cresol was methylated with methanol, using the catalyst of $CeO_2$—MgO—$GeO_2$—$SnO_2$ having a ratio by weight of $CeO_2$ : MgO : $GeO_2$ : $SnO_2$ of 1 : 0.5 : 0.1 : 0.2, prepared in Example 11. The reaction conditions and the results of the reaction are given below:

| | |
|---|---|
| Catalyst used (in volume): | 20 cc |
| Molar ratio of feeds: | methanol/m-cresol = 6 |
| Reaction temperature: | 450°C |
| Gas space velocity: | 1000 hr$^{-1}$ |
| m-Cresol conversion: | 98.4 % |
| 2,3-Xylenol yield: | 1.9 % |
| 2,5-Xylenol yield: | 11.1 % |
| 2,3,6-Trimethylphenol yield: | 78.9 % |
| o-Methylation selectivity: | 93.4 % |
| Methanol utilization efficiency: | 50.6 % |

EXAMPLE 20 p-tert-Butylphenol was methylated with methanol, using the catalyst of $CeO_2$—MgO—$GeO_2$ having a ratio by weight of $CeO_2$ : MgO : $GeO_2$ of 1 : 0.7 : 0.1, prepared in Example 3. The reaction conditions and the results of the reaction are given below:

| | |
|---|---|
| Catalyst used (in volume): | 20 cc |
| Molar ratio of feeds: | methanol/p-tert.-butylphenol = 2 |
| Reaction temperature: | 450°C |
| Gas space velocity: | 1000 hr$^{-1}$ |
| Butylphenol conversion: | 82.2 % |
| 2-Methyl-4-tert.-butylphenol yield: | 65.0 % |
| 2,6-Dimethyl-4-tert.-butylphenol yield: | 12.2 % |
| o-Methylation selectivity: | 94.0 % |
| Methanol utilization efficiency: | 61.3 % |

EXAMPLE 21 p-tert.-Butylphenol was methylated with methanol, using the catalyst of $CeO_2$—MgO—$GeO_2$—$SnO_2$ having a ratio by weight of $CeO_2$ : MgO : $GeO_2$ : $SnO_2$ of 1 : 0.5 : 0.1 : 0.2, prepared in Example 11. The reaction conditions and the results of the reaction are given below:

| | |
|---|---|
| Catalyst used (in volume): | 20 cc |
| Molar ratio of feeds: | Methanol/p-tert.-butylphenol = 2 |
| Reaction temperature: | 450°C |
| Gas space velocity: | 1000 hr$^{-1}$ |
| Butylphenol conversion: | 81.8 % |
| 2-Methyl-4-tert.-butylphenol yield: | 68.4 % |
| 2,6-Dimethyl-4-tert.-butylphenol yield: | 10.1 % |
| o-Methylation selectivity: | 96.0 % |
| Methanol utilization efficiency: | 65.4 % |

What is claimed is:

1. In a process for selective methylation in the ortho position of a phenol represented by the formula:

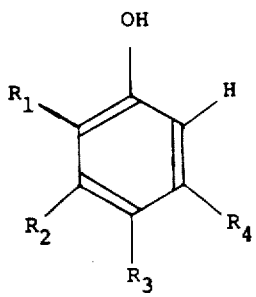

wherein each of $R_1$, $R_2$, $R_3$ and $R_4$ which may be the same or different represents a hydrogen atom or a saturated aliphatic hydrocarbon group having 1 to 6 carbon atoms, comprising reacting at a pressure atmospheres about 0.5 to 20 atomspheres the phenol with methanol in a molar ratio of phenol to methanol of 1:1–15 in the vapor phase at a gas space velocity of 100 to 2000 hr$^{-1}$ and at an elevated temperature between 300° to 500°C in the presence of a catalyst, the improvement which comprises using as said catalyst a catalyst containing cerium oxide, magnesium oxide, germanium oxide and tin oxide in a ratio by weight of $CeO_2$:MgO:$SnO_2$:$GeO_2$=1:0.01–2:0–2:0.01–2.

2. A process according to claim 1, wherein an oxide mixture of rare earth elements containing at least 30 % by weight of cerium oxide is used as the cerium oxide.

3. A process according to claim 1, wherein the weight ratio of cerium oxide to magnesium oxide is 1 : 0.5 - 1.

4. A process according to claim 1, wherein the weight ratio of cerium oxide to germanium oxide is 1 : 0.05 - 1.

5. A process according to claim 1, wherein the weight ratio of cerium oxide to tin oxide is 1 : 0.05 - 1.

6. A process according to claim 1, wherein each of $R_1$, $R_2$, $R_3$ and $R_4$, which may be the same or different represents a hydrogen atom or a saturated aliphatic hydrocarbon group having 1 to 4 carbon atoms.

7. A process according to claim 6, wherein each of $R_1$, $R_2$, $R_3$ and $R_4$, which may be the same or different represents a hydrogen atom or a methyl, ethyl, isopropyl or tert.-butyl group.

8. A process according to claim 1, wherein the phenol to be methylated is phenol, and the product is composed mainly of 2,6-xylenol.

9. A process according to claim 1, wherein the phenol to be methylated is phenol, and the product is composed of o-cresol and 2,6-xylenol.

10. A process according to claim 1, wherein the phenol to be methylated is m-cresol, and the product is composed mainly of 2,3,6-trimethylphenol.

11. A process according to claim 1, wherein the temperature is from 350° to 450°C.

12. A process according to claim 1, wherein the gas space velocity is 200 to 1000 hr$^{-1}$.

13. A process according to claim 1, wherein the catalyst is used in a fixed bed.

14. A process according to claim 1, wherein the catalyst is used in a fluidized bed.

15. A process according to claim 1, wherein a phenol having two hydrogen atoms in the ortho-positions is methylated and the reaction intermediate which is ortho-mono-methylphenol is recycled to the reaction system to produce a product which is an ortho-dimethyl phenol.

16. A process according to claim 1 wherein the molar ratio of phenol to methanol is 1:2–10.

* * * * *